US012766246B2

(12) United States Patent
Nakajima et al.

(10) Patent No.: US 12,766,246 B2
(45) Date of Patent: Oct. 20, 2026

(54) DRUG ADMINISTRATION DEVICE WITH ANNULAR VALVE HAVING SLIT SHAPE OPENING

(71) Applicant: TERUMO KABUSHIKI KAISHA, Tokyo (JP)

(72) Inventors: Kentaro Nakajima, Nakakoma-gun (JP); Ryoji Kobayashi, Hadano (JP); Takehiko Ueda, Kofu (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 503 days.

(21) Appl. No.: 18/469,953

(22) Filed: Sep. 19, 2023

(65) Prior Publication Data

US 2024/0001027 A1 Jan. 4, 2024

Related U.S. Application Data

(63) Continuation of application No. PCT/JP2022/009798, filed on Mar. 7, 2022.

(30) Foreign Application Priority Data

Mar. 24, 2021 (JP) ................................ 2021-050717

(51) Int. Cl.
*A61M 5/142* (2006.01)
*A61M 5/32* (2006.01)

(52) U.S. Cl.
CPC .......... *A61M 5/142* (2013.01); *A61M 5/3287* (2013.01)

(58) Field of Classification Search
CPC ...... A61M 5/142; A61M 5/3287; A61M 5/36; A61M 39/22
See application file for complete search history.

(56) References Cited

U.S. PATENT DOCUMENTS 5,453,097 A 9/1995 Paradis
5,806,831 A 9/1998 Paradis
(Continued)

FOREIGN PATENT DOCUMENTS

JP 2015-215073 A 12/2015
JP 2016-150209 A 8/2016
(Continued)

OTHER PUBLICATIONS

International Search Report issued in the corresponding International Patent Application No. PCT/JP2022/009798, dated May 10, 2022.

(Continued)

*Primary Examiner* — Serkan Akar
(74) *Attorney, Agent, or Firm* — Foley & Lardner LLP

(57) ABSTRACT

A liquid medicine administration device includes: a needle unit configured to be inserted into and placed on a living body; a liquid medicine supply device provided separately from the needle unit and configured to deliver a liquid medicine filled inside from a distal portion; a tube configured to allow the liquid medicine to flow, the tube having a distal end connected to the needle unit; and a connector to which the liquid medicine supply device is attached, the connector being located at a proximal end of the tube. The connector includes: a valve body that has a disk shape and that opens during delivery of the liquid medicine to allow the liquid medicine supply device to communicate with the tube, and a valve seat that is annular and provided on a tube side with respect to the valve body, the valve seat protruding toward and contacting the valve body.

6 Claims, 12 Drawing Sheets

(56) References Cited

U.S. PATENT DOCUMENTS

| | | | | |
|---|---|---|---|---|
| 2010/0276035 | A1* | 11/2010 | Py | A61M 5/1782 141/98 |
| 2014/0073926 | A1* | 3/2014 | Rajendran | A61M 5/142 600/478 |
| 2020/0078581 | A1 | 3/2020 | Toh et al. | |

FOREIGN PATENT DOCUMENTS

| | | | |
|---|---|---|---|
| WO | WO-2012/151542 | A | 11/2012 |
| WO | WO-2018/173962 | A | 9/2018 |

OTHER PUBLICATIONS

Written Opinion of the International Searching Authority issued in the corresponding International Patent Application No. PCT/JP2022/009798, dated May 10, 2022.

* cited by examiner

10

DRUG ADMINISTRATION DEVICE WITH ANNULAR VALVE HAVING SLIT SHAPE OPENING

CROSS-REFERENCE TO RELATED APPLICATIONS

This is a bypass continuation of PCT/JP2022/009798, filed on Mar. 7, 2022, which claims priority to Japanese Application No. 2021-050717, filed on Mar. 24, 2021. The contents of these applications are hereby incorporated by reference in their entireties.

BACKGROUND

The present disclosure relates to a liquid medicine administration device having a device body that is to be attached to and placed on a body surface of a living body.

The applicant of the present application has proposed a liquid medicine administration device for administering a desired dose of a liquid medicine to a living body at an appropriate time (see WO 2018/173962 A).

The liquid medicine administration device described above is connected with, for example, a patch-type tube with needle. The patch-type tube with needle includes a connector connectable to a nozzle of a barrel, a liquid delivery tube that is flexible and connected to the connector, a patch part connected to the other end of the liquid delivery tube and is adherable to a skin of a patient, and a puncture needle protruding from the patch part. The puncture needle is punctured substantially perpendicularly to the skin. Liquid medicine discharged from the barrel is injected into the body of the patient through the tube with needle.

SUMMARY

An object of certain embodiments of the present invention is to provide a liquid medicine administration device capable of stably opening an opening/closing hole of a valve body when a liquid medicine flows.

According to one aspect of the present disclosure, a liquid medicine administration device includes: a needle unit inserted into and placed on a living body; a device body provided separately from the needle unit and capable of delivering a liquid medicine filled inside from a distal portion; a tube that allows the liquid medicine to flow, the tube having a distal end connected to the needle unit; and a connector to which the device body is attached, the connector being provided at a proximal end of the tube. The connector includes: a valve body that has a disk shape and that opens during delivery of the liquid medicine to allow the device body to communicate with the tube, and a valve seat that is annular and provided on a tube side with respect to the valve body, the valve seat protruding toward the valve body so that the valve body comes in contact with the valve seat. The valve body has an opening/closing hole that has a slit shape and that passes through the valve body in an axial direction at a central part. The valve seat has an inclined portion inclined radially inward toward the tube.

According to certain embodiments, a connector is provided at the proximal end of a tube connected to a needle unit that is inserted into and placed on the living body. The connector is provided with a valve body that opens during delivery of a liquid medicine from a device body to allow the device body to communicate with the tube, and an annular valve seat that is provided on the tube side with respect to the valve body. The valve seat protrudes to the valve body so that the valve body contacts the valve seat. The valve body has, at a central part, an opening/closing hole having a slit shape and passing through the valve body in the axial direction, and the valve seat includes an inclined portion inclined radially inward toward the tube.

Therefore, when pressure is applied to the valve body from the liquid medicine delivered from the device body, stress generated on the radially inner side that is the opening/closing hole side is suppressed because the inclined portion of the valve seat with which the valve body comes in contact is inclined radially inward, and accordingly, the deformation amount of the valve body can be suppressed.

As a result, when the liquid medicine flows through the opening/closing hole of the valve body, the deformation amount of the opening/closing hole on the radially inner side of the valve seat is suppressed, whereby the pressure (opening pressure) from the liquid medicine for opening the opening/closing hole does not fluctuate, and the opening/closing hole can be stably opened at a predetermined pressure.

DETAILED DESCRIPTION

A liquid medicine administration device 10 is placed on a body surface of, for example, the abdomen of a patient (living body) and automatically administers a liquid medicine S1 (see FIG. 5) into the body. For example, the liquid medicine administration device 10 is used to administer the liquid medicine S1 to the patient when a predetermined time elapses after a medical treatment for the patient or to gradually administer the liquid medicine S1 over time. The liquid medicine S1 administered by the liquid medicine administration device 10 is not particularly limited, and examples thereof include liquid medicines such as antibody drugs, anticancer agents, chemotherapeutic agents, anesthetics, antibiotics, insulin, blood preparations, and nutrients.

Figure 1:
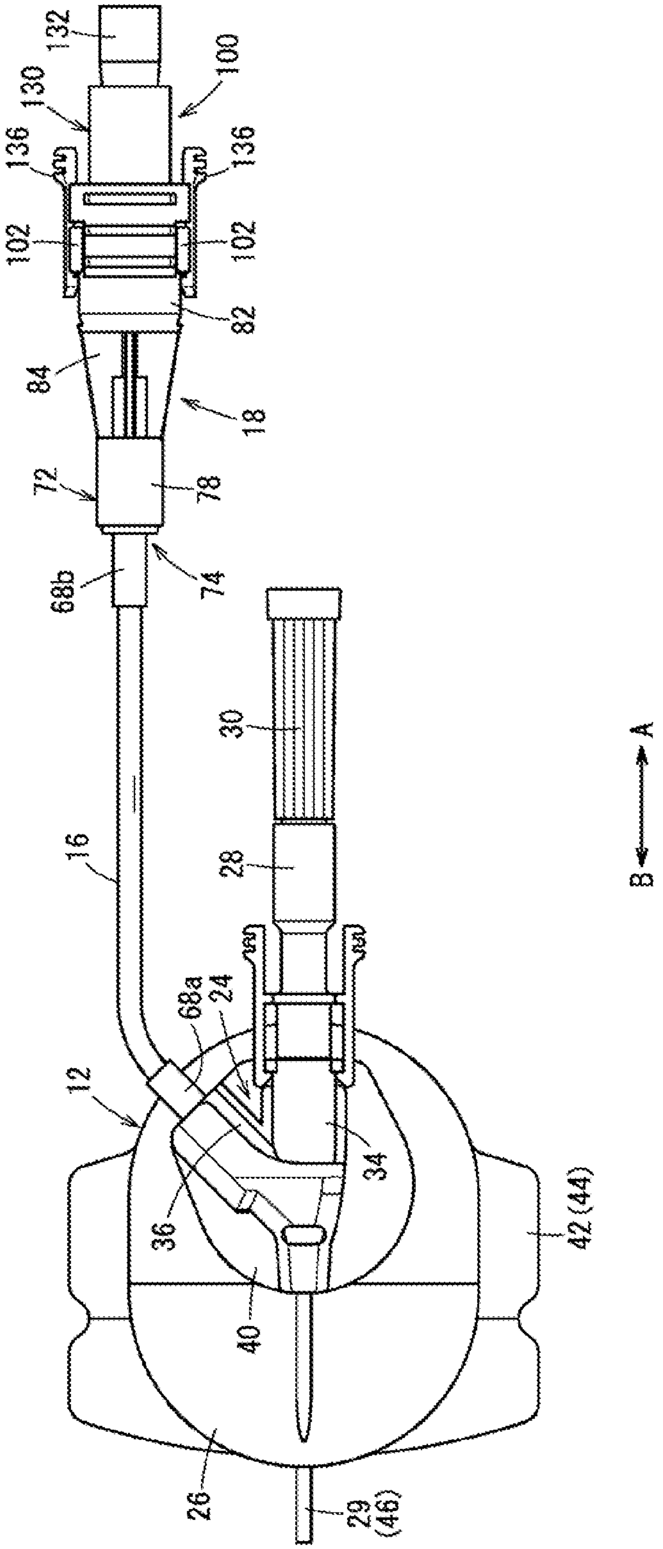
FIG. 1 is an overall plan view of a liquid medicine administration device according to an embodiment of the present invention.
Figure 2:
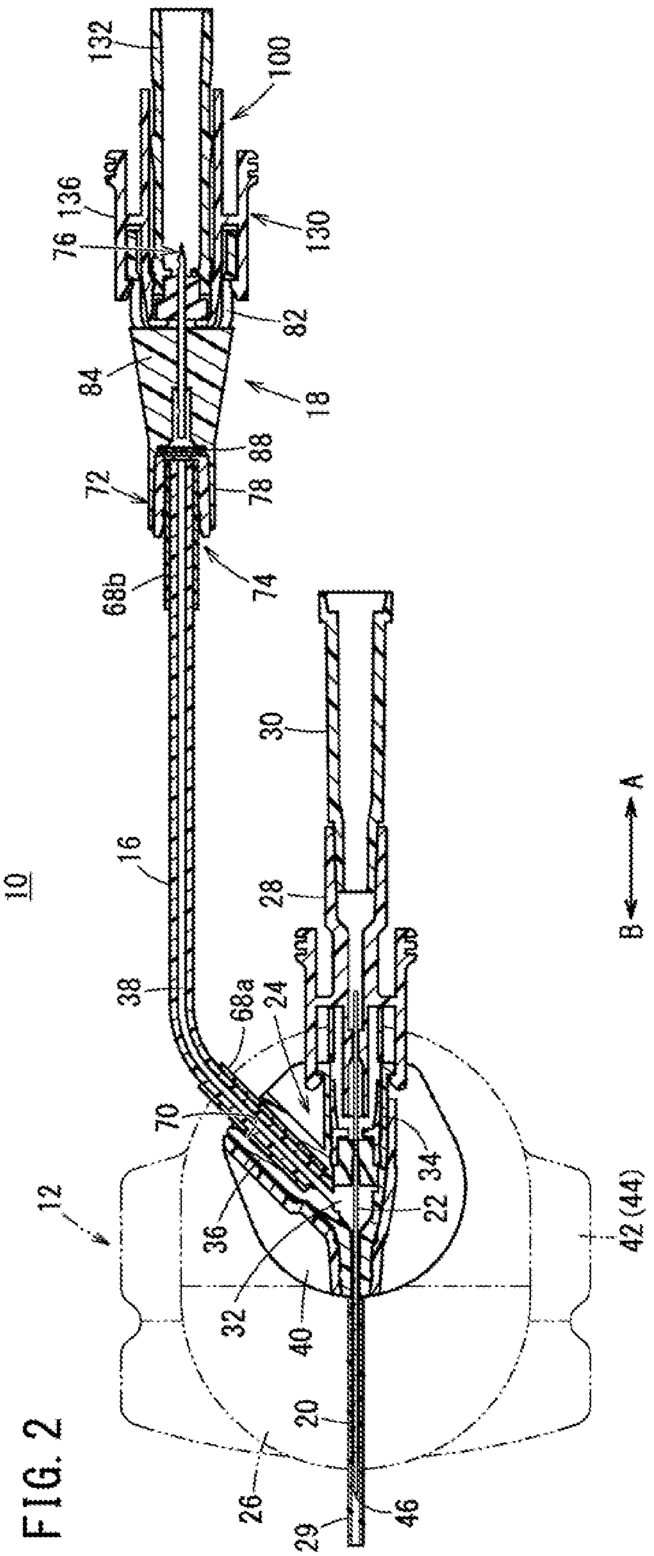
FIG. 2 is an overall cross-sectional view of the liquid medicine administration device illustrated in FIG. 1.
Figure 3:
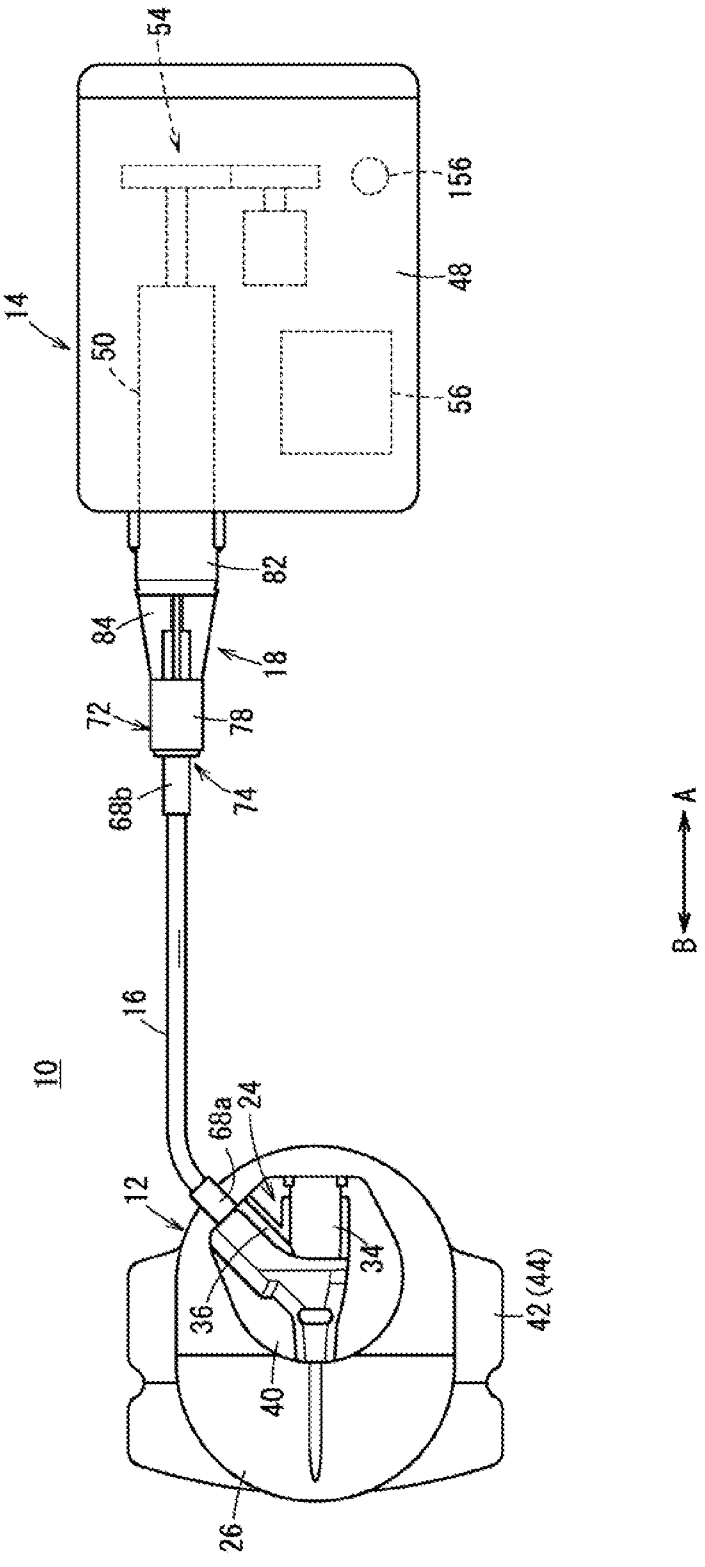
FIG. 3 is an overall plan view illustrating a state in which a device body is attached to a connector unit in the liquid medicine administration device illustrated in FIG. 1.
Figure 4:
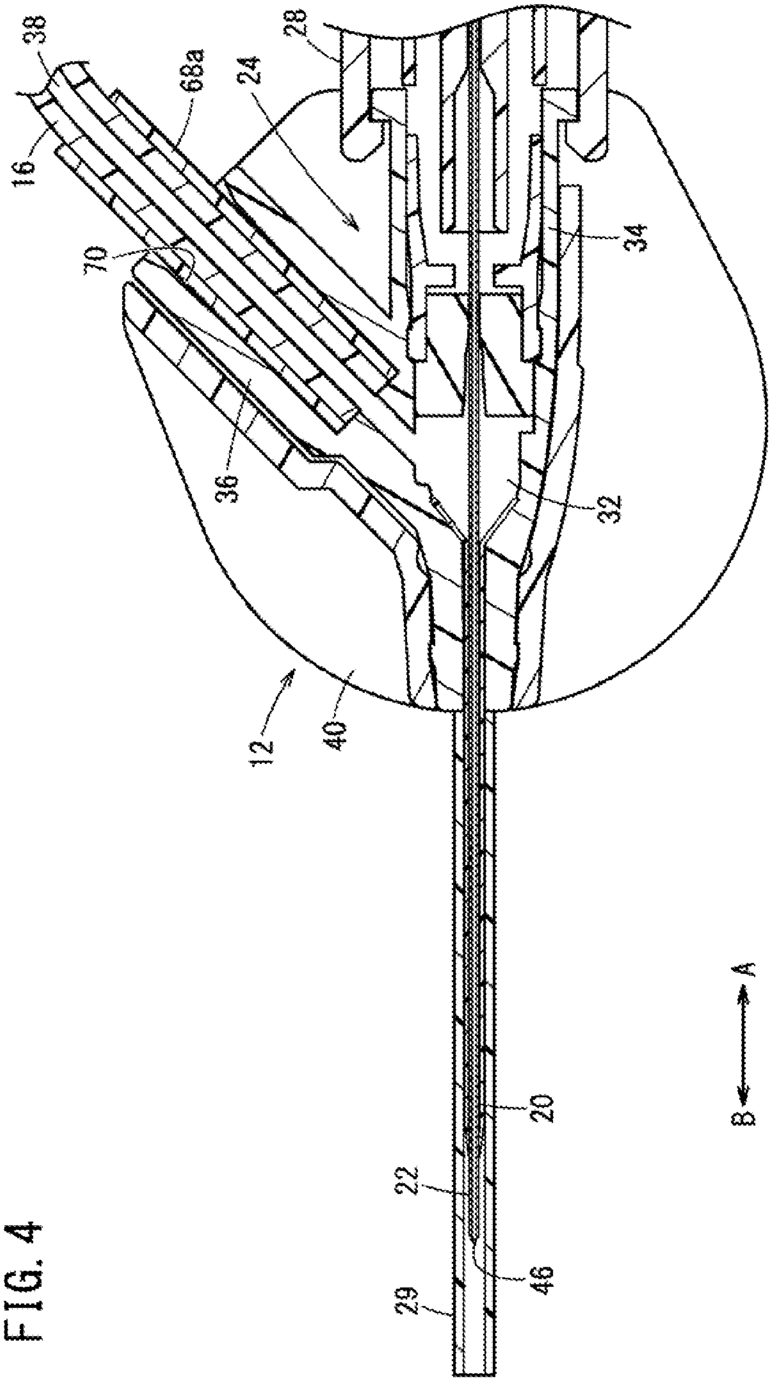
FIG. 4 is an enlarged cross-sectional view of the vicinity of the needle unit in the liquid medicine administration device illustrated in FIG. 2.

As illustrated in FIGS. 1 to 3, the liquid medicine administration device 10 includes a needle unit 12, a device body 14 (a liquid medicine supply device) (see FIG. 3) capable of supplying the liquid medicine S1, a tube 16 that allows the liquid medicine S1 to flow between the needle unit 12 and the device body 14, and a connector unit (connector) 18 that is provided at a proximal end of the tube 16 and to which the device body 14 or the like is selectively connectable. That is, in the liquid medicine administration device 10, the device body 14 and the needle unit 12 are separated from each other and connected to with the tube 16 therebetween.

As illustrated in FIGS. 1 to 4, the needle unit 12 constitutes a unit to introduce the liquid medicine S1 by allowing a catheter 20 to be inserted from the body surface into the body (under the skin) and to be placed into the body, and includes the catheter (outer needle) 20, an inner needle 22 passing through the inside of the catheter 20, a hub 24 that holds a proximal end of the catheter 20 and to which the tube 16 is connected, a sealing body 26 for affixing the hub 24 onto the body surface, a needle hub 28 that is connected to a proximal end of the hub 24 and holds a proximal end of the inner needle 22, and a gripping component 30 attached to a proximal end of the needle hub 28.

The catheter 20 is a flexible tubular body and having a lumen through which the liquid medicine S1 can flow, and protrudes downward from a lower surface (surface facing the body surface) of the hub 24. The lumen communicates with a distal end opening of the catheter 20 and communicates with a space 32 in the hub 24 on the proximal side (direction of arrow A) of the catheter 20 (see FIGS. 2 and 4). A proximal portion of the catheter 20 is crimped and fixed to the hub 24 by, for example, a crimping pin (not illustrated).

The distal side of the inner needle 22 is inserted into the lumen of the catheter 20, and the proximal end thereof is inserted into the hub 24 and held by the distal end of the needle hub 28. The outer peripheral side of a multi-needle 46 in which the catheter 20 and the inner needle 22 overlap is covered with a tubular protector 29.

The hub 24 is formed of, for example, a resin material, and is bifurcated at an intermediate portion between the distal end and the proximal end thereof. The hub 24 has a hub body 34 that linearly extends from the distal end to the proximal side. The hub body 34 has the space 32 that allows the lumen of the catheter 20 to communicate with a flow path 38 of the tube 16. On the other hand, the needle hub 28 to which the gripping component 30 is joined is detachably connected to the proximal end of the hub body 34.

The hub 24 also has a hub branch part 36 that branches at a predetermined angle from the intermediate portion toward the proximal side (direction of arrow A). The distal end of the tube 16 is connected to the proximal end of the hub branch part 36 via an opened inlet port 70, so that the flow path 38 of the tube 16 and the space 32 communicate with each other through the inlet port 70.

Further, a flat hub substrate 40 is formed below the hub 24, and the sealing body 26 is attached to a lower surface of the hub substrate 40. The sealing body 26 is flexible and formed in a sheet shape wider than the hub substrate 40 in the planar direction. An adhesive surface adherable to the body surface is provided on the entire lower surface of the sealing body 26, and a sheet-like backing sheet 42 is attached to the adhesive surface before the needle unit 12 is used.

The backing sheet 42 has a tab 44 that protrudes from the sealing body 26 and can be picked up by a user, and the adhesive surface is exposed when the user picks up the tab 44 and removes the backing sheet 42 from the sealing body 26. The upper surface of the backing sheet 42 to which the sealing body 26 is attached is coated for facilitating removal of the backing sheet from the adhesive surface.

The user of the liquid medicine administration device 10 punctures the body with the multi-needle 46 in which the catheter 20 and the inner needle 22 overlap, and further pulls out the inner needle 22 from the catheter 20 in a punctured state (disengages the needle hub 28 from the needle unit 12 to the proximal side (direction of arrow A)), thereby placing the catheter 20 into the body of the patient.

Figure 5:
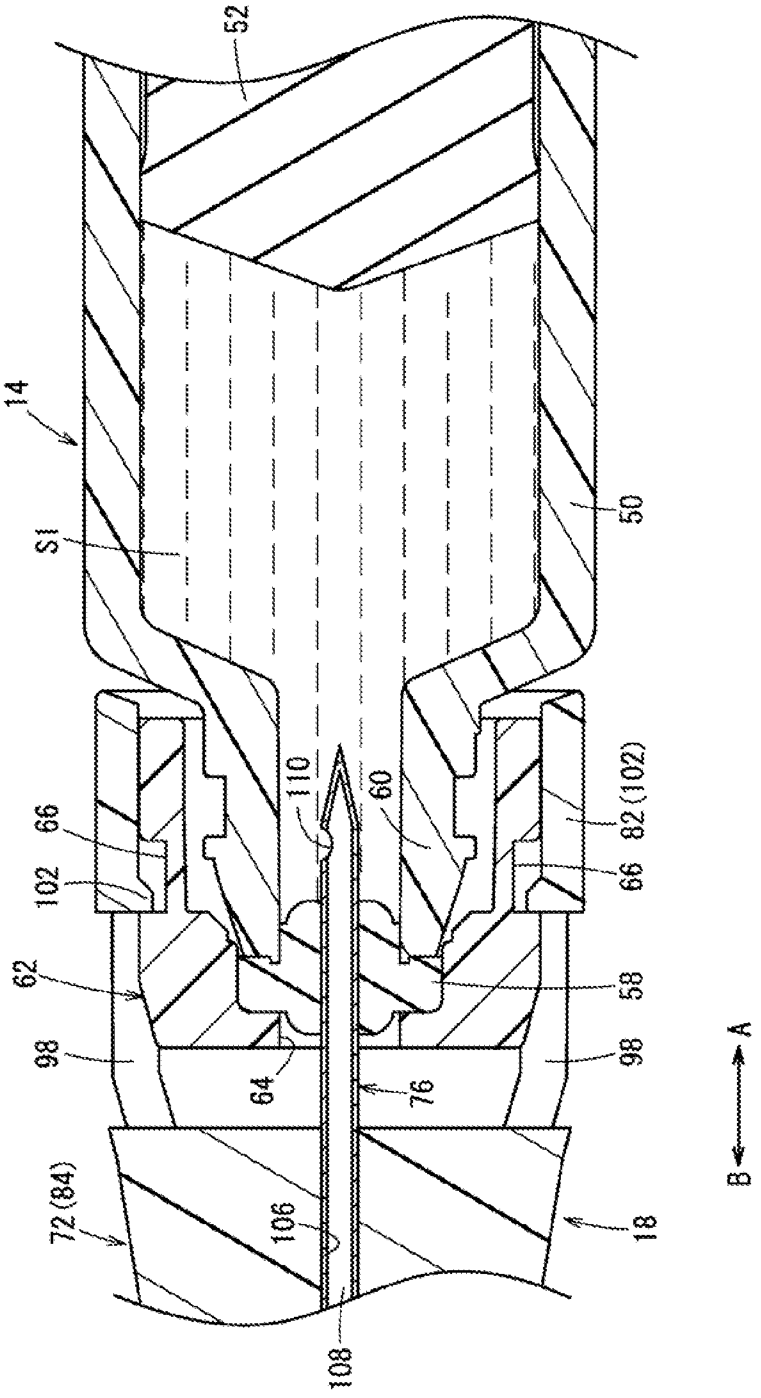
FIG. 5 is an enlarged cross-sectional view illustrating the vicinity of a connection portion of the device body in the liquid medicine administration device illustrated in FIG. 3.

As illustrated in FIGS. 3 and 5, the device body 14 has a function of storing the liquid medicine S1 and delivering the liquid medicine S1 from the distal portion at an appropriate time, and includes a case 48 that has an accommodation space formed inside for accommodating the components. The case 48 includes therein a container 50 that stores the liquid medicine S1, a moving mechanism 54 that moves a first gasket 52 in the container 50, a control unit 56 that controls the operation of the moving mechanism 54, and a power supply unit (not illustrated) that can supply power to each component.

The container 50 is formed in a tubular shape along the axial direction (direction of arrow A, B), and is filled with the liquid medicine S1. A distal portion of the container 50 protrudes in the axial direction (direction of arrow B) by a predetermined length from a distal end of the case 48 and is exposed to the outside.

In addition, the container 50 has an outlet port 60 that is opened at the distal end with a reduced diameter and that is sealed with a packing 58. The packing 58 is sandwiched between a distal end of a cylindrical body-side connector 62 provided to cover the outer peripheral side of the outlet port and the distal end of the container 50. Thus, the liquid medicine S1 is sealed and held in the container 50.

The body-side connector 62 is formed in a cap shape, has a hole 64 through which a hollow needle 76 to be described below can be inserted at the center of the distal end, and has an engagement recess 66 that is recessed radially inward and that is to be engaged with a connector body 72 of the connector unit 18 to be described below on the outer peripheral surface. When the connector body 72 is engaged with the engagement recess 66 of the body-side connector 62, the device body 14 is connected to the proximal side (direction of arrow A) of the connector body 72 via the body-side connector 62.

As illustrated in FIGS. 1 to 4 and 6, the tube 16 is a flexible tube having a predetermined length and having inside the flow path 38 through which the liquid medicine S1 can flow. One end of the tube 16 is fixed to the inlet port 70 of the hub branch part 36 of the hub 24 by an appropriate fixing means such as adhesion, welding, or crimping via a tubular joint tube **68*a* attached to the outer peripheral side of the tube 16. Thus, the flow path 38 of the tube 16 communicates with the space 32 of the hub 24 through the inlet port 70**.

In addition, the other end of the tube 16 is inserted into a tube holder 74 of the connector unit 18 to be described below in a state in which a tubular joint tube **68*b*** is attached to the outer peripheral side, and is fixed by appropriate fixing means such as adhesion, welding, or crimping.

As illustrated in FIGS. 1 to 3 and 5 to 11, the connector unit 18 includes the connector body 72, the tube holder 74 accommodated in the distal part of the connector body 72 (direction of arrow B), and the hollow needle 76 held along the center of the axis in the connector body 72.

The connector body 72 includes, for example, a fixing portion 78 to which the tube 16 is fixed together with the tube holder 74, the fixing portion 78 being formed from a resin material and formed on the distal side (direction of arrow B), a connected portion 82 to which either one of the device body 14 or the syringe 80 is selectively connected, the connected portion 82 being formed on the proximal side (direction of arrow A), and an intermediate portion 84 that connects the fixing portion 78 and the connected portion 82.

The fixing portion 78 is formed in a cylindrical shape opened toward the distal side (direction of arrow B) and has a holder hole 86 into which the tube holder 74 is inserted and fixed and a valve hole 90 that is located proximal to (direction of arrow A) the holder hole 86 and in which the valve body 88 is accommodated. The holder hole 86 is formed in a tapered shape so as to open toward the distal side of the fixing portion 78 and gradually decrease in diameter toward the proximal side (direction of arrow A).

As illustrated in FIGS. 7 to 10, the valve hole 90 has a circular cross section with a reduced diameter with respect to the holder hole 86, and has a predetermined length in the axial direction (direction of arrow A, B). A proximal end face (surface) 90*a* of the valve hole 90 is formed in a circular shape when viewed in the axial direction of the connector body 72 and is orthogonal to the axial direction. A communication chamber 104 described below is opened in a central part of the valve hole 90. In addition, the proximal end face 90*a* of the valve hole 90 has a plurality of protruding portions 92 formed in a protruding shape toward the distal side (direction of arrow B), which is the valve body 88 side, on the radially outer side of the opening portion of the communication chamber 104.

Figure 8:
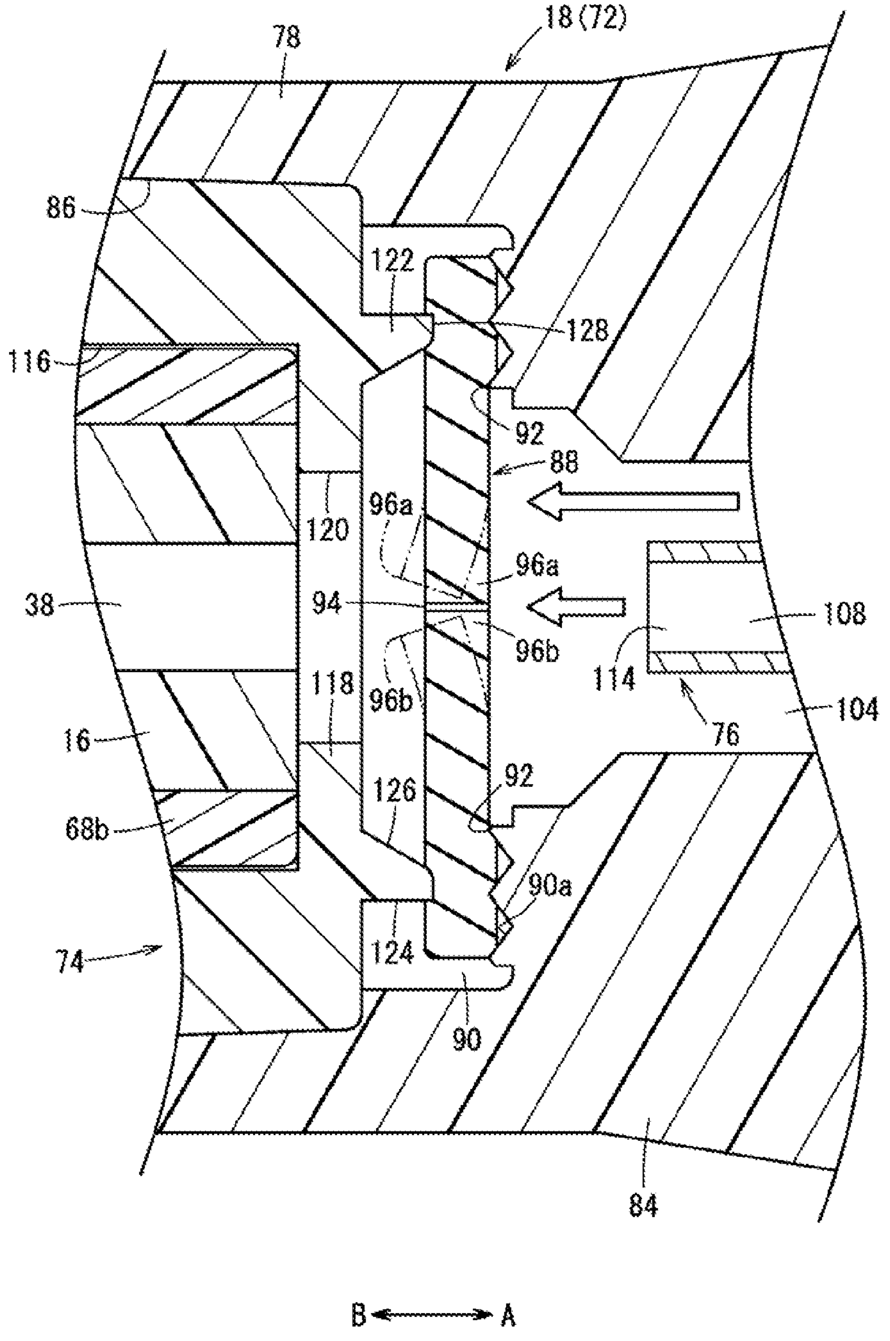
FIG. 8 is a further enlarged cross-sectional view illustrating the vicinity of the valve body in FIG. 7.

For example, when viewed in a direction orthogonal to the axial direction of the connector body 72, the protruding portions 92 have a triangular cross-sectional shape that gradually taper toward the distal side, are arranged in a straight line along the orthogonal direction, and are equally spaced in parallel to each other. In other words, a region between two adjacent protruding portions 92 is formed in a groove shape recessed in a rectangular cross-sectional shape toward the proximal side (direction of arrow A) as illustrated in FIG. 8. The plurality of protruding portions 92 is provided so as to freely come into contact with the upper surface of the valve body 88 accommodated in the valve hole 90.

Figure 9:
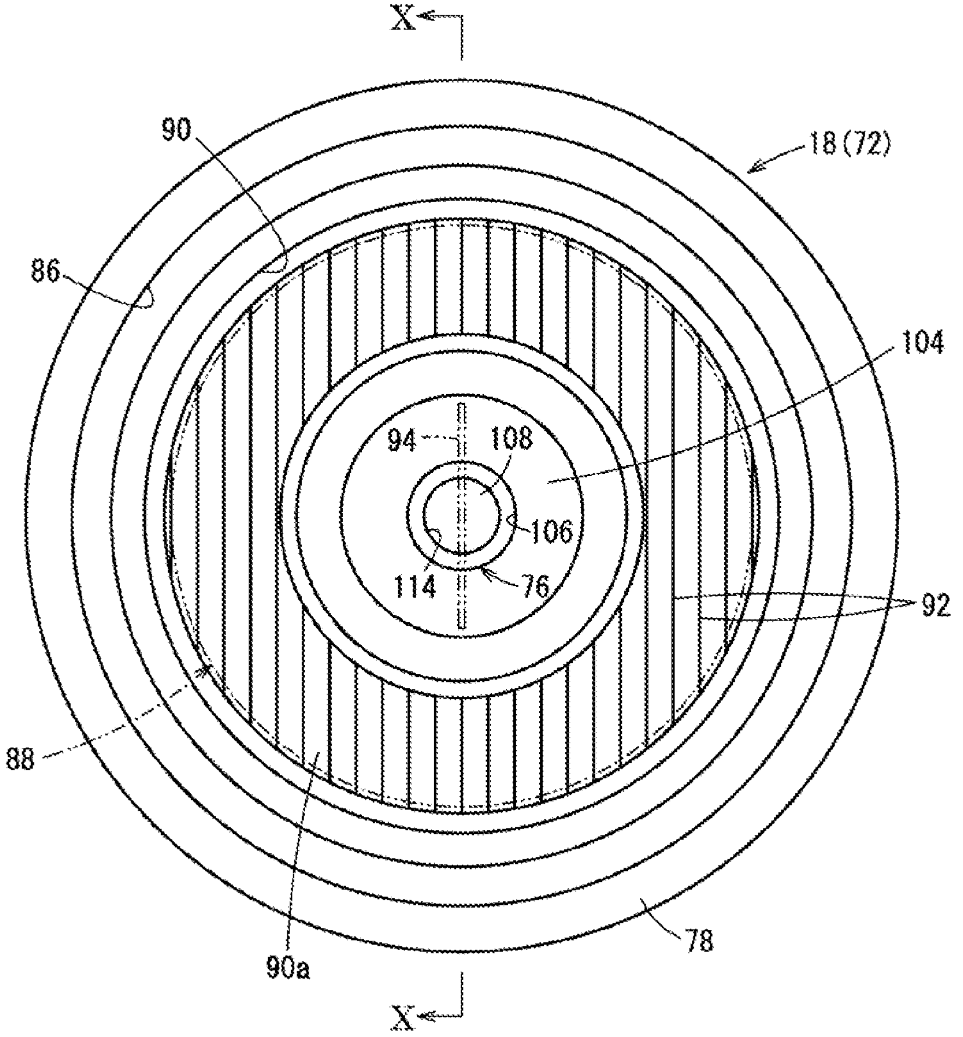
FIG. 9 is a plan view of a connector body constituting the connector unit as viewed from a distal side along an axial direction.

The valve body 88 is formed in a disk shape with a constant thickness from an elastic material such as silicone rubber, for example, and is formed with a linear slit hole (opening/closing hole) 94 illustrated in FIG. 9. The slit hole 94 is formed at a central position when viewed in the thickness direction. The valve body 88 is formed in a thin plate shape in which the dimension (thickness dimension) in the axial direction is smaller than the dimension in the radial direction. The slit hole 94 linearly extends radially outward from the central part of the valve body 88 and passes through the valve body 88 in the thickness direction (direction of arrow A, B in FIG. 8). Note that the slit hole 94 is not limited to being linearly formed (in a slit shape), and may be formed in a cross shape, for example.

The valve body 88 is accommodated in the valve hole 90 so that the slit hole 94 is substantially parallel to the plurality of protruding portions 92 (see FIG. 9) and the distal ends of the protruding portions 92 are in contact with and slightly bites into the upper surface of the valve body 88 (see FIG. 8).

Figure 7:
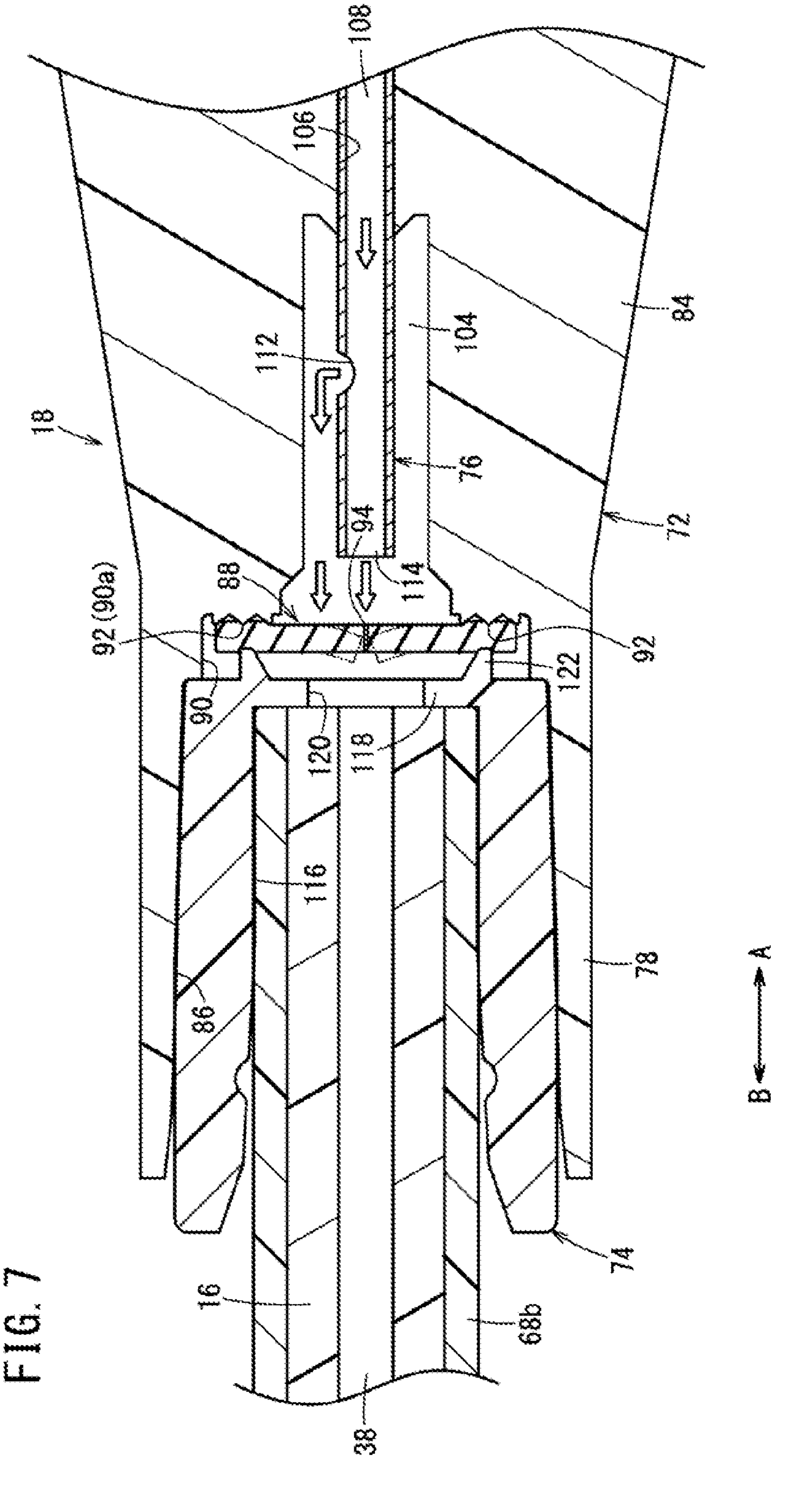
FIG. 7 is an enlarged cross-sectional view illustrating the vicinity of a valve body in FIG. 6.

In addition, as illustrated in FIGS. 7 and 8, when pressure is applied to the upper surface of the valve body 88 toward the distal side (direction of arrow B), a pair of slit pieces 96*a* and 96*b* facing the slit hole 94 and facing each other are elastically deformed so as to be bent toward the distal side, whereby the slit piece 96*a* and the slit piece 96*b* are separated from each other in the radial direction to be in an open state with a gap therebetween (see a shape indicated by a two-dot chain line in FIGS. 7 and 8).

On the other hand, the pair of slit pieces 96*a* and 96*b* is not elastically deformed in a state in which the pressure on the upper surface of the valve body 88 toward the distal side is reduced, and thus, the slit piece 96*a* and the slit piece 96*b* face each other in contact with each other, thereby forming a closed state without having a gap therebetween.

Figure 6:
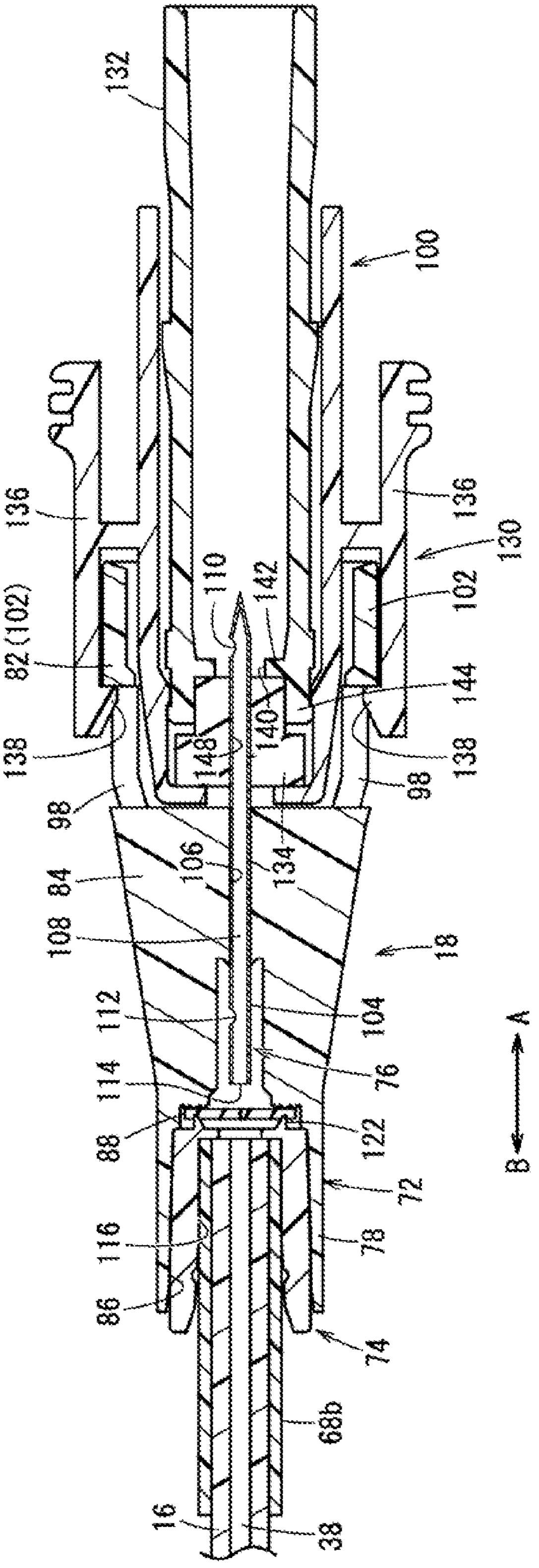
FIG. 6 is an enlarged cross-sectional view illustrating the vicinity of the connector unit in the liquid medicine administration device illustrated in FIG. 2.

As illustrated in FIGS. 5 and 6, the connected portion 82 is formed in a cylindrical shape opened toward the proximal side (direction of arrow A), and has a pair of engagement holes 98 opened in an outer peripheral wall in a rectangular shape. The device body 14 to be connected to the connected portion 82 from the proximal side (direction of arrow A) or connection arms 136 of an adapter member 100 for mounting the syringe 80 is engaged with the pair of engagement holes 98.

Further, the connected portion 82 is provided with a pair of connector claws 102 protruding inward in the radial direction from the inner peripheral surface on the proximal side (direction of arrow A) of the engagement holes 98. When the body-side connector 62 of the device body 14 is connected to the connector body 72, the connector claws 102 are engaged with the engagement recesses 66, whereby the device body 14 is connected to the proximal side (direction of arrow A) of the connector body 72 with the body-side connector 62 in a state in which the relative movement with respect to the connector unit 18 in the axial direction (direction of arrow A, B) is restricted as illustrated in FIG. 5.

As illustrated in FIGS. 6 to 10, the intermediate portion 84 includes the communication chamber 104 that is formed at the center of the axis, opens on the distal side (direction of arrow B) that is the fixing portion 78 side, and communicates with the valve hole 90, and a needle engaging hole 106 that penetrates from the proximal end of the communication chamber 104 to the inside of the connected portion 82. The communication chamber 104 has a constant diameter along the axial direction, extends from the substantially center of the intermediate portion 84 along the axial direction to the distal side, and opens on the proximal end face 90*a* of the valve hole 90 so as to face the valve body 88.

As illustrated in FIGS. 5 to 7, the needle engaging hole 106 has a diameter smaller than that of the communication chamber 104 and can hold the hollow needle 76 when the hollow needle 76 is inserted therein. The hollow needle 76 is provided to connect the device body 14 or the adapter member 100 connected to the connector unit 18 and the communication chamber 104 of the connector body 72, and has a needle hole 108 therein. The hollow needle 76 is held such that one end, which is a sharp end, is exposed inside the connected portion 82 by a predetermined length at the center of the axis through the needle engaging hole 106, and the other end is exposed inside the communication chamber 104 by a predetermined length at the center of the axis through the needle engaging hole 106. That is, the central part of the hollow needle 76 in the axial direction is held by the intermediate portion 84 in the connector body 72, and the one end and the other end of the hollow needle 76 protrude into the connected portion 82 and the communication chamber 104, respectively.

The hollow needle 76 also has a proximal end opening 110 communicating with the needle hole 108 in the vicinity of one end thereof and a side hole 112 communicating with the needle hole 108 in the vicinity of the other end accommodated in the communication chamber 104. The proximal end opening 110 is located inside and communicates with the connected portion 82. The proximal end opening 110 and the side hole 112 are opened on the outer peripheral surface so as to be orthogonal to the axial direction (direction of arrow A, B) of the hollow needle 76.

On the other hand, a distal end opening 114 that opens in the axial direction (direction of arrow B) and communicates with the needle hole 108 is opened at the other end of the hollow needle 76. The distal end opening 114 is disposed inside the communication chamber 104 so as to be apart from the valve body 88 toward the proximal side (direction of arrow A) by a predetermined distance and face the slit hole 94. That is, the side hole 112 is formed in the hollow needle 76 at a position intermediate between the proximal end opening 110 and the distal end opening 114.

As illustrated in FIGS. 2 and 5 to 8, the tube holder 74 is formed in a bottomed cylindrical shape having an open distal end, and an outer peripheral surface thereof has a tapered shape having a diameter gradually reduced from the distal end toward the proximal side (direction of arrow A). The tube holder 74 is inserted into and engaged with the holder hole 86 of the connector body 72. Thus, the tube holder 74 is coaxially fixed.

In addition, the tube holder 74 has a tube hole 116 that is open to the distal side (direction of arrow B) and that extends in the axial direction. The other end of the tube 16 to which the joint tube **68*b* is attached is inserted into the tube hole 116 and fixed by an appropriate fixing means such as adhesion, welding, or crimping. The flow path 38 of the tube 16 is opened to the proximal side (direction of arrow A) inside the holder hole 86**.

Furthermore, a bottom wall 118 serving as the proximal end of the tube holder 74 is formed in a circular shape extending in a direction orthogonal to the axial direction (direction of arrow A, B). The bottom wall 118 has a through hole 120 formed in the central part so as to penetrate in the axial direction and communicate with the flow path 38 of the tube 16, and an annular valve seat 122 protruding from the proximal end of the bottom wall 118 on the outside of the through hole 120 in the radial direction.

Figure 10:
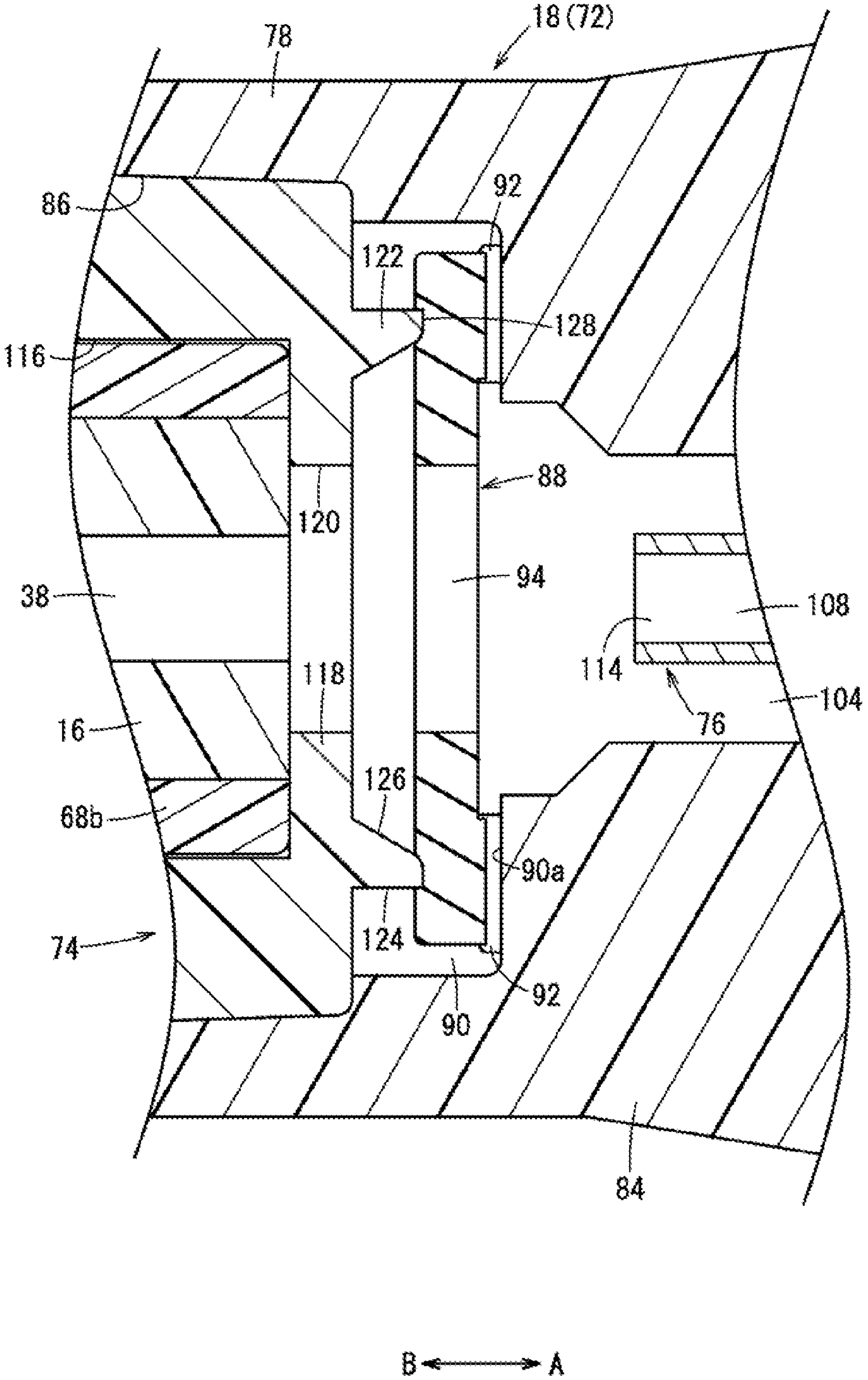
FIG. 10 is a cross-sectional view taken along a line X-X in FIG. 9.

As illustrated in FIGS. 7, 8, and 10, the valve seat 122 protrudes from the bottom wall 118 by a predetermined height, and has an outer peripheral surface 124 orthogonal to the bottom wall 118, and an inner peripheral surface (inclined portion) 126 having a tapered shape inclined radially outward as it extends in a direction away from the bottom wall 118 (to the proximal side). That is, the valve seat 122 is formed in an inner tapered shape in which the radially inner side is formed in a tapered shape.

The valve seat 122 has a valve seat surface 128 that is formed substantially parallel to the bottom wall 118 and to which the lower surface of the valve body 88 is contactable on the proximal side (direction of arrow A) of the outer peripheral surface 124 and the inner peripheral surface 126. The valve seat surface 128 is formed to be flat along the radial direction. In other words, the inner peripheral surface 126 is inclined radially inward as it extends in a direction away from the valve seat surface 128, that is, to the distal side (direction of arrow B).

The valve seat 122 described above is provided so as to be located radially outside the slit hole 94 when the valve body 88 comes in contact with the valve seat surface 128 as illustrated in FIG. 10. That is, the valve seat 122 is disposed at a position not overlapping the slit hole 94.

Then, as illustrated in FIGS. 8 and 10, the lower surface of the valve body 88 comes in contact with and slightly bites into the valve seat 122 to the proximal side at a position on the outer peripheral side of the slit hole 94, and thus, the valve body 88 is held in a state of being tightened in the axial direction (direction of arrow A, B) between the proximal end face **90*a* of the valve hole 90 and the valve seat 122**.

As illustrated in FIGS. 1, 2, 6, 11, and 12, the adapter member 100 includes an adapter body 130 that has an cylindrical shape and is attached when the syringe 80 for priming a priming solution S2 (physiological saline) is attached to the connector unit 18, a syringe connector 132 that is inserted into the adapter body 130, and a seal member 134 that is accommodated in the adapter body 130 on the distal side of the syringe connector 132.

The adapter body 130 has a tapered shape such that the distal end thereof gradually decreases in diameter toward the distal side (direction of arrow B) so as to be insertable into the connected portion 82 of the connector body 72. The adapter body 130 also has a pair of connection arms 136 extending to the distal side on the outer peripheral side at the central part in the axial direction.

The connection arms 136 are symmetrical with respect to the center of the axis of the adapter body 130. Each of the connection arms 136 is parallel to the outer peripheral surface of the adapter body 130 and is separated radially outward from the outer peripheral surface of the adapter body 130 via a leg part at the central part along the axial direction. Each of the connection arms 136 has a claw 138 protruding toward the adapter body 130 at the distal end.

When the adapter member 100 is connected to the connector body 72, the claws 138 of the connection arms 136 are engaged with the engagement holes 98 of the connected portion 82, so that the relative movement in the axial direction (direction of arrow A, B) and the rotational direction are restricted, and the adapter member 100 is connected to the proximal side (direction of arrow A) of the connected portion 82 and fixed.

The syringe connector 132 has a cylindrical shape having a diameter smaller than that of the adapter body 130, and is integrally fixed by, for example, being press-fitted into the adapter body 130. The syringe connector 132 has a partition wall 142 formed on the distal side (direction of arrow B) so as to be perpendicular to the axial direction, the partition wall 142 having an insertion hole 140 at the center (see FIG. 6).

The syringe connector 132 also has a holding end 144 capable of holding the seal member 134 at a position distal to the partition wall 142. The holding end 144 is open to the distal side (direction of arrow B). The seal member 134 is integrally held such that the proximal side is inserted into and held by the holding end 144, and the outer peripheral surface is engaged with the inner peripheral surface of the adapter body 130.

Figure 11:
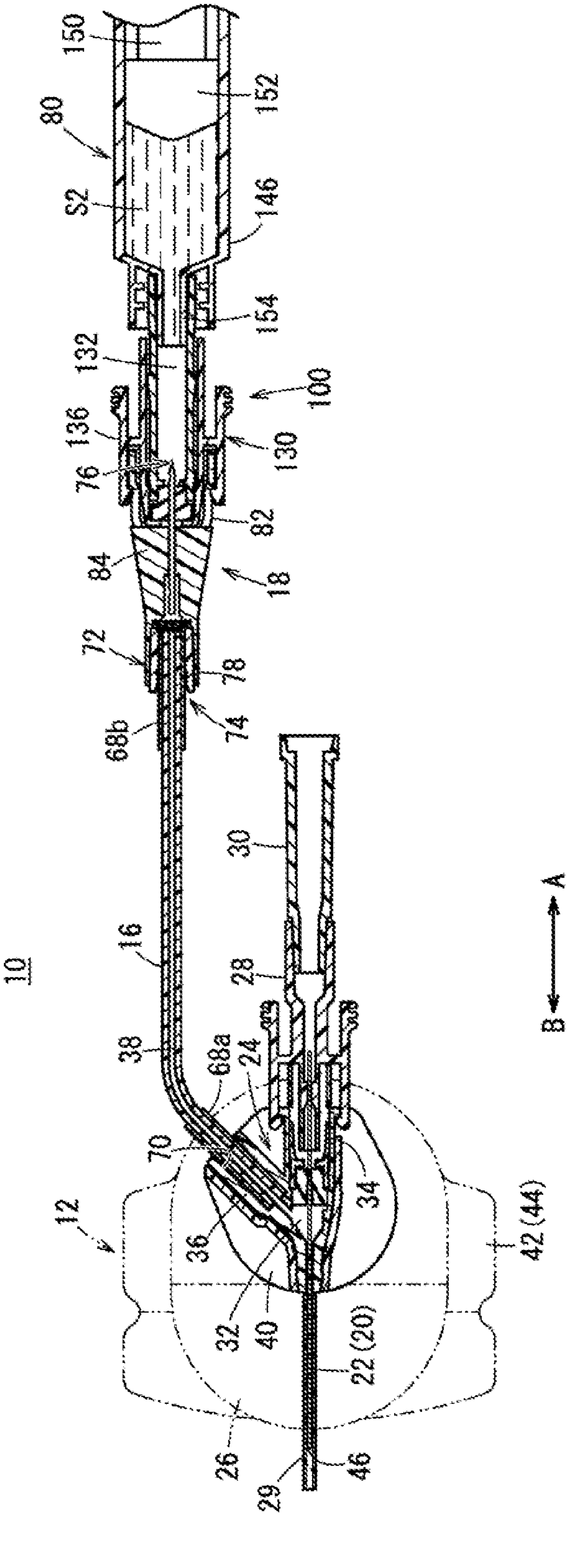
FIG. 11 is an overall cross-sectional view illustrating a state in which a syringe is attached to the connector unit in the liquid medicine administration device illustrated in FIG. 2.
Figure 12:
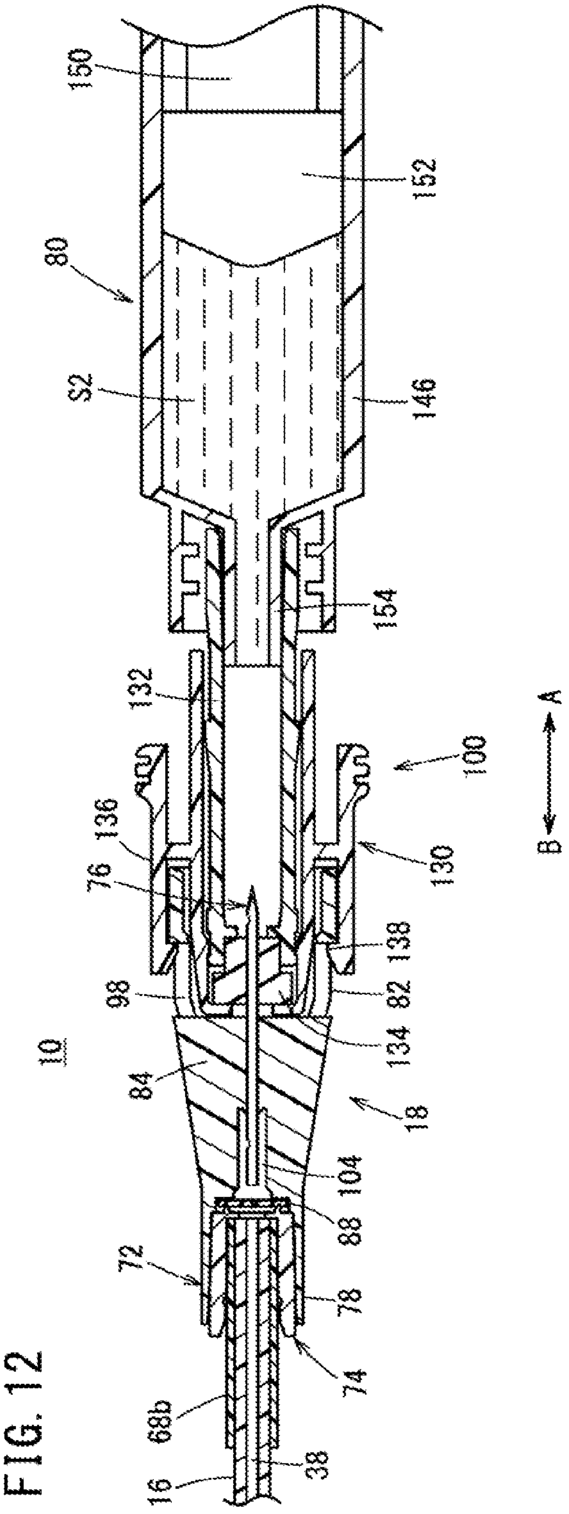
FIG. 12 is an enlarged cross-sectional view illustrating the vicinity of the connector unit and the syringe in the liquid medicine administration device illustrated in FIG. 11.

As illustrated in FIGS. 11 and 12, a distal portion of a barrel 146 constituting the syringe 80 and filled with the priming solution S2 is connected to the proximal end of the syringe connector 132.

The seal member 134 is formed of, for example, an elastic material such as rubber, has a circular cross section when viewed in the axial direction, and has a needle insertion hole 148 into which the hollow needle 76 is inserted, the needle insertion hole 148 passing through the seal member 134 in the axial direction at the center of the axis. Then, as illustrated in FIG. 6, when the adapter member 100 is connected to the connector body 72, one end of the hollow needle 76 exposed inside the connected portion 82 is inserted into the insertion hole 140 through the needle insertion hole 148, so that the hollow needle 76 protrudes to the proximal side (direction of arrow A) of the seal member 134 through the through hole 120 inside the syringe connector 132, and the space between the hollow needle 76 and the syringe connector 132 is sealed by the seal member 134.

The proximal end opening 110 of the hollow needle 76 is located in and communicates with the syringe connector 132, and the side hole 112 and the distal end opening 114 of the hollow needle 76 are located in and communicates with the communication chamber 104 of the connector body 72. That is, the communication chamber 104 of the connector body 72 and the inside of the syringe connector 132 are connected and communicates with each other by the hollow needle 76.

The liquid medicine administration device 10 according to the embodiment of the present invention is basically configured as described above, and operation and effects will be described below.

When the liquid medicine administration device 10 is used, the needle unit 12 and the tube 16 are placed on the body surface of the patient, the syringe 80 is connected to fill the inside of the catheter 20 with the priming solution S2, and then the device body 14 is connected to automatically administer the liquid medicine S1 to the patient under the control of the control unit 56.

First, as illustrated in FIGS. 11 and 12, the user connects the syringe 80 filled with the priming solution S2 to the connector unit 18 of the liquid medicine administration device 10. Specifically, the user inserts the distal end of the syringe 80 into the syringe connector 132 of the connector unit 18 from the proximal side, whereby the inside of the barrel 146 of the syringe 80 and the inside of the syringe connector 132 communicate with each other.

Then, the first priming for filling the tube 16 and the needle unit 12 of the liquid medicine administration device 10 with the priming solution S2 is performed.

First, when the user grips a rod 150 of the syringe 80 and pushes the rod 150 toward the distal side (direction of arrow B), a second gasket 152 attached to the distal end of the rod 150 moves to the distal side along the barrel 146, and accordingly, the priming solution S2 filled in the barrel 146 is discharged from a discharge port 154 opened at the distal end of the barrel 146 to the inside of the syringe connector 132.

Then, as illustrated in FIG. 7, the priming solution S2 flows into the needle hole 108 through the proximal end opening 110 of the hollow needle 76 opened inside the syringe connector 132, flows in the axial direction (direction of arrow B), and is introduced into the communication chamber 104 of the connector body 72 through the distal end opening 114 with a portion thereof being introduced into the communication chamber 104 from the needle hole 108 through the side hole 112.

That is, a portion of the priming solution S2 is guided to the distal side (direction of arrow B) to the communication chamber 104 through the distal end opening 114 along the axial direction, and at the same time, the remaining portion is guided radially outward through the side hole 112, and then, flows in the axial direction (direction of arrow B) along the inner peripheral surface of the communication chamber 104. In other words, the priming solution S2 is guided to the communication chamber 104 in two directions through the distal end opening 114 and the side hole 112 having different opening directions.

The upper surface of the valve body 88 is pressed to the distal side (direction of arrow B) by the priming solution S2 supplied into the communication chamber 104, and the pair of slit pieces 96*a* and 96*b* is elastically deformed so as to be bent toward the distal side, whereby the slit hole 94 is opened in the radial direction, and the priming solution S2 flows toward the tube holder 74 (direction of arrow B) through the slit hole 94 and flows to the flow path 38 of the tube 16 through the through hole 120.

At this time, the pressure applied from the priming solution S2 to the upper surface of the valve body 88 is suitably distributed into a pressure applied to the vicinity of the central part of the valve body 88 from the priming solution S2 introduced through the distal end opening 114 and a pressure applied to the vicinity of the outer edge of the valve body 88 from the priming solution S2 introduced through the side hole 112 and then flowing along the inner peripheral surface of the communication chamber 104. Therefore, the application of the pressure to the vicinity of the central part of the valve body 88 having the slit hole 94 is reduced as compared to a configuration in which the pressure due to the priming solution S2 that is introduced only through the distal end opening 114 of the hollow needle 76 is applied only to the vicinity of the central part of the valve body 88.

As a result, even when the pressure of the priming solution S2 is rapidly applied to the valve body 88, the load on the slit hole 94 is reduced, and thus, the situation in which the slit hole 94 remains opened due to the vicinity of the slit hole 94 being plastically deformed can be avoided. In a state in which the pressure from the priming solution S2 is not applied, the slit hole 94 can be reliably closed with the vicinity of the slit hole 94 being restored to the original shape by elasticity. That is, when the flow of the priming solution S2 is completed, it is possible to reliably close the slit hole 94 and block the communication between the communication chamber 104 and the tube 16.

In other words, due to the configuration in which the hollow needle 76 has the side hole 112 through which the priming solution S2 is introduced in addition to the distal end opening 114 through which the priming solution S2 is introduced, a pressure loss is generated when the priming solution S2 flows, and the internal pressure of the priming solution S2 in the communication chamber 104 is suitably distributed. Thus, the pressure applied to the upper surface of the valve body 88 can be distributed in the radial direction.

Further, when the priming solution S2 flows into the communication chamber 104 and the slit hole 94 is opened, a force for separating the slit pieces 96*a* and 96*b* defining both sides of the slit hole 94 from each other—that is, a force for pressing the slit pieces 94*a* and 96*b* radially outward—is applied to the valve body 88. However, the upper surface of the valve body 88 is in contact with and slightly bites into the plurality of protruding portions 92 extending in the direction orthogonal to the force in the radial direction, whereby the movement of the valve body 88 in the radial direction is restricted. Therefore, the valve body 88 is maintained at a predetermined position in the valve hole 90 so that the valve body 88 is located on the axis of the connector body 72. In other words, the frictional resistance of the valve body 88 with respect to the connector body 72 is increased to restrict the movement in the radial direction by bringing the valve body 88 into contact with the plurality of protruding portions 92.

When the valve body 88 is biased to the distal side (direction of arrow B) by the pressure of the priming solution S2, stress is generated on the lower surface (contact surface) of the valve body 88 in contact with the valve seat surface 128 of the valve seat 122 at a boundary portion between the outer peripheral surface 124 and the inner peripheral surface 126. Although the outer peripheral surface 124 is upright along the application direction (direction of arrow B) in which the pressure is applied, that is, the axial direction toward the distal side, the inner peripheral surface 126 is inclined radially inward with respect to the application direction. Therefore, the stress generated on the inner peripheral surface 126 side can be suppressed relative to the stress generated on the outer peripheral surface 124 side. As a result, when the valve body 88 is pressed toward the distal side (direction of arrow B) under the action of supplying the priming solution S2, the deformation amount on the inner peripheral side of the valve seat 122 can be suppressed relative to the deformation amount on the outer peripheral side of the valve seat 122.

As a result, when the priming solution S2 flows through the slit hole 94 of the valve body 88, the opening degree of the slit hole 94 provided on the inner peripheral side of the valve seat 122 can be maintained substantially constant, so that the slit hole 94 can be stably opened by a predetermined pressure applied to the valve body 88, and the priming solution S2 can be supplied toward the needle unit 12 at a stable flow rate. In other words, the opening pressure due to the priming solution S2 for opening the slit hole 94 does not fluctuate, and the slit hole 94 can be reliably opened with a substantially constant pressure at all times.

Then, the priming solution S2 flowing from the connector body 72 to the flow path 38 of the tube 16 flows into the space 32 of the hub 24 through the inlet port 70 and flows into the catheter 20, whereby the tube 16, the space 32 of the hub 24, and the inside of the catheter 20 are filled with the priming solution S2. Thus, the first priming is completed. In addition, when the flow of the priming solution S2 through the slit hole 94 of the valve body 88 is stopped and the pressure applied to the valve body 88 is reduced, the slit pieces 96*a* and 96*b* that have been elastically deformed return to the original shapes, and the slit hole 94 is closed. Accordingly, communication between the communication chamber 104 of the connector body 72 and the tube 16 is blocked.

Next, the user grips and positions the needle unit 12 at a desired position on the body surface, and then removes the protector 29 from the multi-needle 46 to the distal side (direction of arrow B). Then, the user punctures the body with the multi-needle 46 protruding from the lower surface of the hub 24, removes the backing sheet 42 by picking up the tab 44 from the sealing body 26 fixed to the needle unit 12, and attach the adhesive surface of the sealing body 26 to the body surface. Thus, the needle unit 12 is fixed to the body surface.

After the puncture, the user relatively pulls out the needle hub 28 and the gripping component 30 to the proximal side (direction of arrow A) from the needle unit 12 to release the engagement between the needle hub 28 and the hub 24, and pulls out the inner needle 22 held by the needle hub 28 from the catheter 20 as illustrated in FIG. 3. At this time, the needle unit 12 attached to the sealing body 26 is maintained in a state of being fixed to the body surface. The placement of the needle unit 12 is completed by the detachment of the inner needle 22 from the needle unit 12.

Next, the second priming for filling the tube 16 and the needle unit 12 of the liquid medicine administration device 10 with the priming solution S2 is performed. The second priming is performed using the priming solution S2 remaining in the syringe 80 used in the first priming. Since the second priming is the same as the first priming, the detailed description thereof will be omitted.

By performing the second priming described above, backflow of blood, cells, and the like from the body surface punctured by the catheter 20 is suitably prevented by the priming solution S2 filled in the tube 16 and the catheter 20, by which clogging of the catheter 20 and the tube 16 due to coagulation of the blood and the like is prevented.

After the second priming is completed, the syringe 80 is removed from the connector unit 18 together with the adapter member 100, and the device body 14 is mounted. Specifically, after the claws 138 of the connection arms 136 of the adapter body 130 are detached outward from the engagement holes 98 of the connector body 72, the syringe 80 is pulled out together with the adapter body 130 to the proximal side (direction of arrow A), whereby the adapter member 100 and the syringe 80 are removed from the connector unit 18.

When the device body 14 is attached to the connector unit 18 described above, first, the body-side connector 62 of the device body 14 is inserted into the connector body 72 (connected portion 82) of the connector unit 18, so that one end of the hollow needle 76 is punctured into the packing 58 at the center of the axis and inserted into the outlet port 60 filled with the liquid medicine S1 as illustrated in FIG. 5. Further, the connector claws 102 are engaged with the engagement recesses 66, so that the device body 14 is connected to the connector unit 18 with the relative movement in the axial direction (direction of arrow A, B) being restricted as illustrated in FIG. 3.

Then, after turning on a power switch 156 provided on the case 48 to activate the liquid medicine administration device the user places the liquid medicine administration device on the body surface with the sealing body provided on the lower surface. After placing the liquid medicine administration device 10 on the body surface, the user waits until an administration start time has come, and at the administration start time, the user moves the first gasket 52 to the distal side (direction of arrow B in FIG. 5) of the container 50 by the moving mechanism 54 under the control of the control unit 56, thereby starting automatic administration of the liquid medicine S1 in the container 50 to the patient.

As described above, when a predetermined time elapses after the liquid medicine administration device 10 is placed on the body surface and the time to administer the liquid medicine S1 has come, the moving mechanism 54 in the device body 14 is driven by a control signal from the control unit 56, so that the first gasket 52 is pressed to the distal side (direction of arrow B) in the container 50. Thus, the liquid medicine S1 is pushed to the distal side by the first gasket 52, and accordingly, the liquid medicine S1 flows into the needle hole 108 through the proximal end opening 110 of the hollow needle 76 located in the outlet port 60 and flows toward the connector body 72 (direction of arrow B) along the needle hole 108.

Then, as illustrated in FIG. 7, the liquid medicine S1 is introduced into the communication chamber 104 of the connector body 72 from the needle hole 108 of the hollow needle 76 through the distal end opening 114 and the side hole 112. At this time, the liquid medicine S1 is guided to the communication chamber 104 from the distal end opening 114 to the distal side (direction of arrow B) along the axial direction, and at the same time, guided radially outward through the side hole 112. In other words, the liquid medicine S1 is guided to the communication chamber 104 from the hollow needle 76 in two different directions.

When the upper surface of the valve body 88 is biased to the distal side (direction of arrow B) by the liquid medicine S1 supplied to the communication chamber 104, stress is generated on the lower surface of the valve body 88 in contact with the valve seat 122 at a boundary portion between the outer peripheral surface 124 and the inner peripheral surface 126. The inner peripheral surface 126 is inclined radially inward, and thus, the stress generated on the inner peripheral surface 126 side can be suppressed relative to the stress generated on the outer peripheral surface 124 side. Therefore, when the valve body 88 is pressed to the distal side (direction of arrow B) under the action of supplying the liquid medicine S1, the slit hole 94 is elastically deformed and opened radially outward with the deformation amount on the inner peripheral side being suitably suppressed relative to the deformation amount on the distal side on the outer peripheral side of the valve seat 122.

As a result, when the liquid medicine S1 flows through the slit hole 94 of the valve body 88, the opening degree of the slit hole 94 provided on the inner peripheral side of the valve seat 122 can be maintained substantially constant, so that the slit hole 94 can be stably opened by a predetermined pressure applied to the valve body 88, and the liquid medicine S1 can be supplied to the tube holder 74 side and to the flow path 38 of the tube 16 through the through hole 120. In other words, the opening pressure due to the liquid medicine S1 for opening the slit hole 94 does not fluctuate, and the slit hole 94 can be reliably opened with a substantially constant pressure at all times.

The liquid medicine S1 flowing along the tube 16 flows from the space 32 to the inside of the catheter 20 through the inlet port 70 of the hub 24, and then is administered into the body punctured with the catheter 20. In addition, when the flow of the liquid medicine S1 through the slit hole 94 of the valve body 88 is stopped after the completion of the administration of the liquid medicine S1 into the body and the pressure applied to the valve body 88 by the liquid medicine S1 is reduced, the slit pieces 96*a* and 96*b* that have been elastically deformed return to the original shapes by elasticity, and the slit hole 94 is closed.

In addition, when being shipped as a product, the above-described liquid medicine administration device 10 is sterilized by circulating a sterilization gas (for example, ethylene oxide gas) therein. The sterilization gas is supplied into the syringe connector 132 of the connector unit 18 on the proximal side in the state illustrated in FIG. 1 where the adapter member 100 is attached to the connector unit 18. As a result, the sterilization gas flows from the syringe connector 132 to the needle hole 108 through the proximal end opening 110 of the hollow needle 76, then flows from the distal end opening 114 and the side hole 112 into the communication chamber 104 of the connector body 72, and flows into the valve hole 90.

The plurality of protruding portions 92 formed in the valve hole 90 extends along the same direction. Thus, the sterilization gas flows radially outward along a groove between the adjacent protruding portions 92, and flows to the tube holder 74 side around the outer peripheral side of the valve body 88. As a result, even when the plurality of protruding portions 92 is provided on the proximal end face 90*a* of the valve hole 90, the sterilization gas can be circulated through the valve body 88, the valve hole 90 in which the valve body 88 is accommodated, and the tube holder 74, and thus, sterilization can be reliably performed.

As described above, in the present embodiment, the liquid medicine administration device 10 includes the connector unit 18 to which the device body 14 capable of delivering the liquid medicine S1 is connected at the proximal end of the tube 16 connected to the needle unit 12 that is inserted into and placed on the patient, the connector unit 18 including the valve body 88 that opens during delivery of the liquid medicine S1 to allow the device body 14 to communicate with the tube 16, and the annular valve seat 122 that protrudes toward the valve body 88 (direction of arrow A, proximal side), and with which the valve body 88 comes in contact, the valve seat 122 being provided distal to (direction of arrow B) the valve body 88, that is, on the tube 16 side.

The valve body 88 is formed from an elastic material, is formed in a thin disk shape, and has the slit hole 94 in the central part. On the other hand, the valve seat 122 includes the valve seat surface 128, which is provided on the radially outer side with respect to the slit hole 94 and with which the valve body 88 comes in contact, the inner peripheral surface 126 that is formed on the slit hole 94 side (radially inner side) with respect to the valve seat surface 128, and the outer peripheral surface 124 that is formed on the opposite side (radially outer side) from the slit hole 94 with respect to the valve seat surface 128. The inner peripheral surface 126 is inclined radially inward toward the tube 16 (direction of arrow B).

Therefore, when the liquid medicine S1 is supplied to the communication chamber 104 of the connector unit 18 from the device body 14, and the pressure of the liquid medicine S1 is applied to the upper surface of the valve body 88, the stress generated on the inner peripheral surface 126 side that is the slit hole 94 side is suppressed because the inner peripheral surface 126 on the slit hole 94 side of the valve seat 122 with which the valve body 88 comes in contact is inclined radially inward toward the tube 16 (direction of arrow B), and accordingly, the deformation amount during the elastic deformation of the valve body 88 on the inner peripheral side can be suppressed relative to the deformation amount on the outer peripheral surface 124 side.

As a result, when the liquid medicine S1 flows through the slit hole 94 of the valve body 88, the opening degree of the slit hole 94 provided on the inner peripheral side of the valve seat 122 can be maintained substantially constant, so that the slit hole 94 can be stably opened by a predetermined pressure applied to the valve body 88, and the liquid medicine S1 can be supplied toward the needle unit 12 at a stable flow rate. In other words, the opening pressure for opening the slit hole 94 does not fluctuate, and the slit hole 94 can be reliably opened with a substantially constant pressure at all times.

In addition, the outer peripheral surface 124 of the valve seat 122 is substantially orthogonal to the lower surface of the valve body 88 that comes in contact with the valve seat 122, and thus, when pressure is applied to the upper surface of the valve body 88, stress can be concentrated on the outer peripheral surface 124 side that is opposite to the slit hole 94, while stress on the inner peripheral surface 126 side that is the slit hole 94 side can be suppressed.

In addition, the connector body 72 constituting the connector unit 18 has the proximal end face 90*a* that faces the valve seat surface 128 of the valve seat 122 and with which the valve body 88 comes in contact, and the valve body 88 is held between the proximal end face 90*a* and the valve seat 122, whereby the valve body 88 can be reliably and easily held inside the connector body 72.

It is obvious that the liquid medicine administration device according to the present invention is not limited to the abovementioned embodiment, and can employ various configurations without departing from the scope of the present invention.

The invention claimed is:

1. A liquid medicine administration device comprising:
a needle unit configured to be inserted into and placed on a living body;
a liquid medicine supply device provided separately from the needle unit and configured to deliver a liquid medicine filled inside from a distal portion;
a tube configured to allow the liquid medicine to flow, the tube having a distal end connected to the needle unit; and
a connector to which the liquid medicine supply device is attached, the connector being located at a proximal end of the tube, wherein the connector comprises:
a valve body that has a disk shape and that is configured to open during delivery of the liquid medicine to allow the liquid medicine supply device to communicate with the tube,
a valve seat that is annular and provided on a tube side with respect to the valve body, the valve seat protruding toward the valve body so that the valve body contacts the valve seat, and
a connector body having an inner peripheral surface, at least a portion of the valve body and the valve seat received by the connector body; wherein:
the valve body has an opening/closing hole that has a slit shape and that passes through the valve body in an axial direction at a central part;
the valve seat has an inclined portion inclined radially inward toward the tube, the valve seat is located at a position on a radially outer side with respect to the opening/closing hole, and has a valve seat surface that the valve body contacts, an inner peripheral surface located on an opening/closing hole side with respect to the valve seat surface, and an outer peripheral surface located on a side opposite to the opening/closing hole with respect to the valve seat surface;
the inclined portion is formed on the inner peripheral surface of the valve seat; and
a space is formed between the outer peripheral surface of the valve seat and the inner peripheral surface of the connector body.

2. The liquid medicine administration device according to claim 1, wherein the valve body is formed of an elastic material, and has a shape in which a dimension in an axial direction of the connector is smaller than a dimension in a radial direction of the connector.

3. The liquid medicine administration device according to claim 1, wherein the outer peripheral surface is orthogonal to a contact surface of the valve body that contacts the valve seat.

4. The liquid medicine administration device according to claim 1, wherein the connector has a surface that faces a valve seat surface of the valve seat and with which the valve body comes in contact, and the valve body is held between the surface and the valve seat.

5. A liquid medicine administration device comprising:
a needle unit comprising:
a catheter,
an inner needle passing through an inside of the catheter,
a hub that holds a proximal end of the catheter, and
a sealing body configured to affix the hub to a body surface;
a liquid medicine supply device comprising a container configured to store a liquid medicine;
a tube configured to receive the liquid medicine from the liquid medicine supply device, the tube having a distal end connected to the hub; and
a connector to which the liquid medicine supply device is attached, the connector being located at a proximal end of the tube, wherein the connector comprises:
a valve body that has a disk shape and that is configured to open during delivery of the liquid medicine to allow the liquid medicine supply device to communicate with the tube,
a valve seat that is annular and provided on a tube side with respect to the valve body, the valve seat protruding toward the valve body so that the valve body contacts the valve seat, and
a connector body having an inner peripheral surface, at least a portion of the valve body and the valve seat received by the connector body; wherein:
the valve body has an opening/closing hole that has a slit shape and that passes through the valve body in an axial direction at a central part;
the valve seat has an inclined portion inclined radially inward toward the tube, the valve seat is located at a position on a radially outer side with respect to the opening/closing hole, and has a valve seat surface that the valve body contacts, an inner peripheral surface located on an opening/closing hole side with respect to the valve seat surface, and an outer peripheral surface located on a side opposite to the opening/closing hole with respect to the valve seat surface;
the inclined portion is formed on the inner peripheral surface of the valve seat; and
a space is formed between the outer peripheral surface of the valve seat and the inner peripheral surface of the connector body.

6. A liquid medicine administration device comprising:
a needle unit configured to be inserted into and placed on a living body;
a tube configured to allow a liquid medicine to flow, the tube having a distal end connected to the needle unit; and
a connector configured to be connected to a liquid medicine supply device, the connector being located at a proximal end of the tube, wherein the connector comprises:
a valve body that has a disk shape and that is configured to open during delivery of the liquid medicine to allow the liquid medicine supply device to communicate with the tube,
a valve seat that is annular and provided on a tube side with respect to the valve body, the valve seat protruding toward the valve body so that the valve body contacts the valve seat, and
a connector body having an inner peripheral surface, at least a portion of the valve body and the valve seat received by the connector body; wherein:
the valve body has an opening/closing hole that has a slit shape and that passes through the valve body in an axial direction at a central part;

the valve seat has an inclined portion inclined radially inward toward the tube, the valve seat is located at a position on a radially outer side with respect to the opening/closing hole, and has a valve seat surface that the valve body contacts, an inner peripheral surface located on an opening/closing hole side with respect to the valve seat surface, and an outer peripheral surface located on a side opposite to the opening/closing hole with respect to the valve seat surface;

the inclined portion is formed on the inner peripheral surface of the valve seat; and a space is formed between the outer peripheral surface of the valve seat and the inner peripheral surface of the connector body.

* * * * *